United States Patent [19]
Yanai et al.

[11] Patent Number: 5,194,381
[45] Date of Patent: Mar. 16, 1993

[54] FELINE INTERFERON AND PROCESS FOR PRODUCTION THEREOF

[75] Inventors: Akira Yanai; Yoshizumi Ueda; Toru Sakurai; Masahiro Satoh, all of Kamakura, Japan

[73] Assignee: Toray Industries, Inc., Tokyo, Japan

[21] Appl. No.: 544,504

[22] Filed: Jun. 27, 1990

[30] Foreign Application Priority Data

Jun. 29, 1989 [JP] Japan ................................. 1-167415

[51] Int. Cl.$^5$ ...................... C12N 15/20; C12N 15/86
[52] U.S. Cl. ............................. 435/172.3; 435/320.1; 935/32
[58] Field of Search .................. 435/91, 172.3, 235, 435/320.1; 536/27

[56] References Cited

FOREIGN PATENT DOCUMENTS 0088622 9/1983 European Pat. Off. .
0175852 4/1986 European Pat. Off. .
0322870 7/1989 European Pat. Off. .

OTHER PUBLICATIONS

Yamamoto et al., *Vet. Immunol. Immunopath.*, vol. 11, 1986, pp. 1–19.
Kozak, *Cell* vol. 44, 1986, pp. 283–292.
Horiuchi et al., Agricultural and Biological Chemistry, vol. 51, No. 6, pp. 1573–1580 (1987).
Maeda et al., *Nature*, vol. 315, No. 6020, pp. 592–594 (1985).

*Primary Examiner*—Richard A. Schwartz
*Assistant Examiner*—James Ketter
*Attorney, Agent, or Firm*—Birch, Stewart, Kolasch & Birch

[57] ABSTRACT

A recombinant silkworm nuclear polyhedrosis virus containing DNA coding for a protein of feline interferon; the recombinant virus is constructed by cotransfection a recombinant plasmid having a gene coding for a protein of feline interferon and a silkworm nuclear polyhedrosis virus DNA into established silkworm cells, and cloning the desired recombinant virus. The recombinant virus is useful for a mass-production of feline interferon.

16 Claims, 7 Drawing Sheets

Fig. 4 pBmFeIFN1      5'......CCTATAGATCCCCAATGGCG......3' pBmFeIFN2-1       ......CCTAAATATGGCG......

pBmFeIFN2-2       ......CCTATAATATGGCG......

pBmFeIFN2-3       ......CCTATAAATATGGCG......

Fig. 6

```
         10         20         30         40         50
TGTGACCTGC CTCAGACCCA CGGCCTGCTG AACAGGAGGG CCTTGACGCT      50
 C  D  L  P  Q  T  H  G  L  L  N  R  R  A  L  T  L        17

60         70         80         90        100
CCTGGGACAA ATGAGGAGAC TCCCTGCCAG CTCCTGTCAG AAGGACAGAA     100
 L  G  Q  M  R  R  L  P  A  S  S  C  Q  K  D  R  N        34

110        120        130        140        150
ATGACTTCGC CTTCCCCCAG GACGTGTTCG GTGGAGACCA GTCCCACAAG     150
 D  F  A  F  P  Q  D  V  F  G  G  D  Q  S  H  K           51

160        170        180        190        200
GCCCAAGCCC TCTCGGTGGT GCACGTGACG AACCAGAAGA TCTTCCACTT     200
 A  Q  A  L  S  V  V  H  V  T  N  Q  K  I  F  H  F        68

210        220        230        240        250
CTTCTGCACA GAGGCGTCCT CGTCTGCTGC TTGGAACACC ACCCTCCTGG     250
 F  C  T  E  A  S  S  S  A  A  W  N  T  T  L  L  E        85

260        270        280        290        300
AGGAATTTTG CACGGGACTT GATCGGCAGC TGACCCGCCT GGAAGCCTGT     300
 E  F  C  T  G  L  D  R  Q  L  T  R  L  E  A  C          102

310        320        330        340        350
GTCCTGCAGG AGGTGGAGGA GGGAGAGGCT CCCCTGACGA ACGAGGACAT     350
 V  L  Q  E  V  E  E  G  E  A  P  L  T  N  E  D  I       119

360        370        380        390        400
TCATCCCGAG GACTCCATCC TGAGGAACTA CTTCCAAAGA CTCTCCCTCT     400
 H  P  E  D  S  I  L  R  N  Y  F  Q  R  L  S  L  Y       136

410        420        430        440        450
ACCTGCAAGA GAAGAAATAC AGCCCTTGTG CCTGGGAGAT CGTCAGAGCA     450
 L  Q  E  K  K  Y  S  P  C  A  W  E  I  V  R  A          153

460        470        480        490        500
GAAATCATGA GATCCTTGTA TTATTCATCA ACAGCTTGC AGAAAAGATT      500
 E  I  M  R  S  L  Y  Y  S  S  T  A  L  Q  K  R  L       170

510
AAGGAGCGAG                                                 513
 R  S  E                                                  174
```

FELINE INTERFERON AND PROCESS FOR PRODUCTION THEREOF

BACKGROUND OF THE INVENTION

1. Field of the Invention

The present invention relates to a recombinant silkworm virus containing feline interferon (FeIFN) gene, FeIFN produced by using the recombinant virus, and a process for the mass-production of FeIFN in which the primary structure of the protein is derived from feline genetic information, as a medicine (antiviral drug) by a gene manipulation technology.

2. Description of the Related Art

An interferon is a physiologically active substance whose main ingredient is a protein showing an antiviral activity, and is abbreviated as IFN. Much literature on the interferon has been published; for example, Reference 1.

The continuing progress made in gene manipulation technology has made possible the mass-production of not only human IFN but also IFN's of animals such as cattle, horses, and dogs, etc., and as a result, exploitative researches into the use of IFN as a remedy for viral diseases, tumors, etc., are underway with respect to some animals.

With respect to felines, interferon-α, -β, and -γ have been reported (Reference 1), but there has been no report that the mass-production of a feline IFN is possible by the application of gene manipulation.

Many feline viral diseases are known, and include feline AIDS, feline leukemia, feline viral rhinotracheitis, feline caliciviral disease, and feline infectious peritonitis, and a report has been made on a case in which the life of a cat infected with feline leukemia virus (FeLV) was prolonged by the oral administration of human IFN-α or bovine IFN-β. If the IFN is administered not orally but by an internal injection, however, it is feared that the production of a neutralizing antibody against a heterologous IFN will occur, although a more striking effect is expected. If a homologous IFN, i.e., FeIFN, becomes readily available, it is expected that the FeIFN will be able to be used as an antiviral agent and an antitumor agent for felines.

SUMMARY OF THE INVENTION

In view of the above circumstances, the present inventors carried out in-depth investigations into the possibilities of mass-producing an FeIFN, and as a result, prepared a feline cDNA library by using a commercially available plasmid vector, from which they successfully isolated a plasmid capable of producing an FeIFN by a transient expression of simian cultured cells. Furthermore, the inventors succeeded in preparing a recombinant virus constructed by recombining a DNA of the silkworm virus with a DNA coding for FeIFN, proliferating the recombinant virus in established silkworm cells or in the body of silkworm, and simply mass-producing the FeIFN.

Accordingly, the present invention provides a recombinant silkworm virus wherein the silkworm virus is recombinant with a DNA coding for the protein of FeIFN.

The present invention also provides a process for the production of a recombinant silkworm nuclear polyhedrosis virus, comprising the step of cotransfecting an established silkworm cell with a recombinant plasmid containing a gene coding for the protein of FeIFN and a silkworm nuclear polyhedrosis virus DNA.

The present invention further provides a process for the production of FeIFN, comprising the step of growing the recombinant silkworm nuclear polyhedrosis virus.

The present invention also provides FeIFN prepared by the above-mentioned process. Furthermore, the present invention provides a process for the purification of FeIFN, comprising the steps of purifying the FeIFN by column chromatography

BRIEF EXPLANATION OF THE DRAWINGS

FIG. 4 represents 5' -terminal nucleotide sequences including a initiation codon ATG of DNAs coding for the FeIFN and present in the recombinant plasmids pBmFeIFN1, pBmFeIFN2-1, pBmFeIFN-2-2, and pBmFeIFN2-3;

FIG. 6 represents a nucleotide sequence coding for the FeIFN and a corresponding amino acid sequence of the FeIFN.

DESCRIPTION OF THE PREFERRED EMBODIMENTS

A cDNA library is prepared according to a conventional procedure using $E.$ $coli$ as a host, poly(A)+RNA as a substrate, and a reverse transcriptase.

As a source of poly(A)+RNA, feline cells, for example, established cultured cells such as LSA (Reference 1) are conveniently used, although other cells may be used. To obtain poly(A)+RNA from cultured cells, the yield of poly(A)+RNA is conveniently improved by selecting an interferon inducer suitable for the cells, and applying the inducer to the cells. For example, for LSA cells, NDV (new castle-disease virus) or TPA (12-O-tetradecanoylphorbol 13-acetate) is used as an inducer during the culturing of the cell, whereby the yield of poly(A)+RNA is remarkably increased. As a plasmid vector, a vector having an expression mechanism for animal cells and capable of representing in $E.$ $coli$ cells, for example, a commercially available vector such as Okayama-Berg vectors from Pharmacia, can be conveniently used. As the host cells, $E.$ $coli$ K12 cells may be used.

Figure 1:
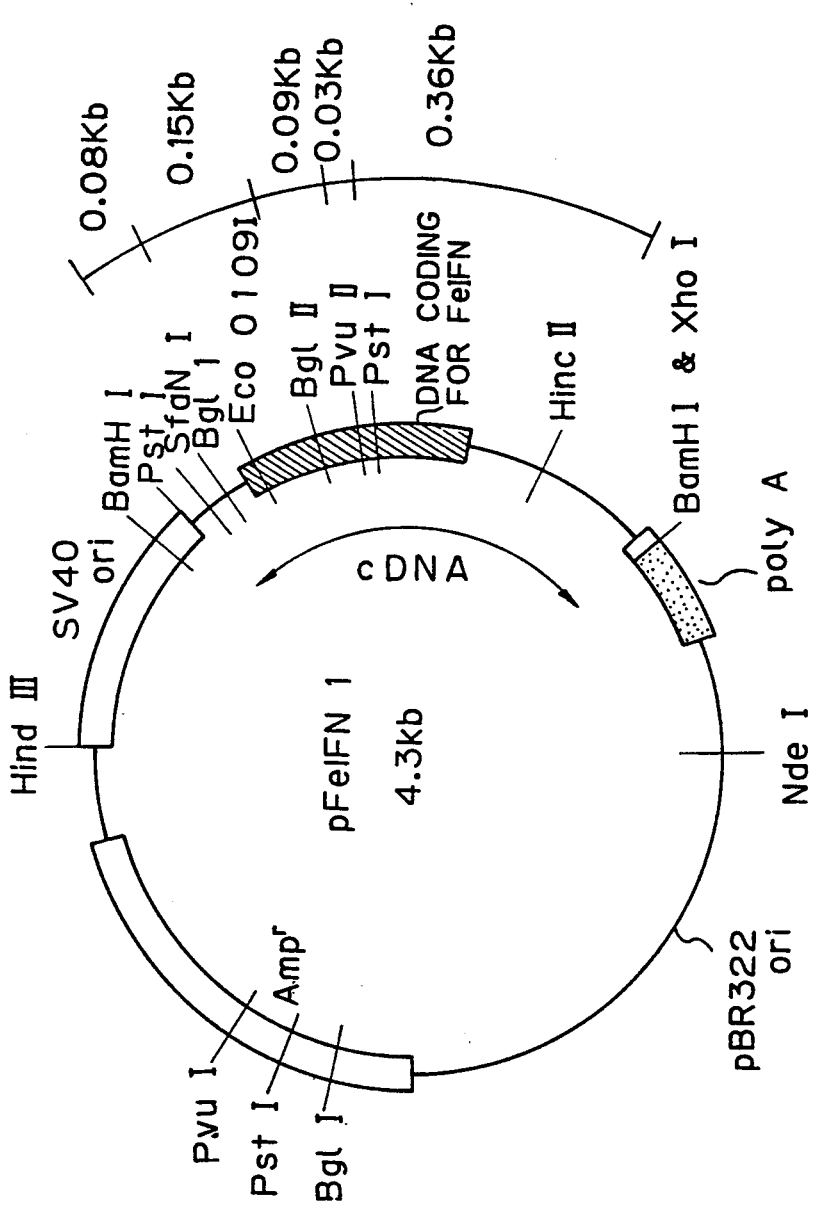
FIG. 1 represents a restriction map of plasmid pFeIFN1 comprising a DNA coding for the protein of FeIFN.

To clone the plasmid containing cDNA coding for the FeIFN, a cDNA is screened by using it to transfect simian established cells COS1 or COS7 and selecting a plasmid which provides the COS1 or COS7 cells with an ability to express an anti-viral activity by transient expression. The transient expression of the FeIFN by a plasmid can be carried out by a conventional procedure such as the DEAE-dextran method or calcium phosphate method. A plasmid thus selected and having a desired activity is pFeIFN1, and $E.$ $coli$ transformed with this plasmid was deposited with the Fermentation Research Institute Agency of Industrial Science and Technology (FRI), on Dec. 23, 1987, as *E. coli* (pFeIFN1) FERM BP-1633). The plasmid pFeIFN1is 4.3 kb in size, and has a restriction map as shown in FIG. 1.

A recombinant silkworm nuclear polyhedrosis virus of the present invention can be constructed as follows. A plasmid is extracted from *E. coli* (pFeIFN1 ), DNA coding for FeIFN protein is removed from the plasmid, and the DNA is inserted into a cloning vector for silkworm (Reference 2) to prepare a recombinant plasmid. Next, the recombinant plasmid is cotransfected with silkworm nuclear polyhedrosis virus DNA into established silkworm cells, to construct the recombinant virus. Accordingly, the present recombinant virus can be constructed in-vivo.

More specifically plasmid pFeIFN1 is extracted from *E. coli* transformant FERM BP-1633 by a conventional procedure as described in Reference 3, a DNA coding for FeIFN is removed from the plasmid, and inserted downstream of an expression control region of a cloning vector for silkworm, such as pBM030 (Reference 2), to construct a recombinant plasmid. This recombinant plasmid and silkworm nuclear polyhedrosis virus DNA (Reference 2) are cotransfected into established silkworm cells such as BM-N cells (Reference 2), which are then continuously cultured to obtain a culture medium containing a non-recombinant (wild type) virus and a recombinant virus. The recombinant virus is cloned by a conventional procedure such as a limiting dilution method or plaque method. Since recombinant virus does not have the ability to form polyhedra, it can be easily distinguished from a wild type virus.

To produce FeIFN, the recombinant silkworm nuclear polyhedrosis virus is cultured in established silkworm cells or in the body of a silkworm.

Where established silkworm cells are used, BM-N cells are inoculated to a culture medium containing the above-mentioned recombinant virus, and the cells are cultured by plate culture or suspension culture. BM-N cells, for example, TC-10 medium (Reference 4) supplemented withfetal bovine serum, are cultured at a temperature of, preferably, 25° C. to 28° C., and after the culturing, the culture broth is centrifuged to obtain a supernatant from which FeIFN is recovered.

Where the body of a silkworm is used, a culture medium containing the above-mentioned recombinant virus is injected into silkworms, which are then kept on mulberry leaves or artificial feed. After the keeping, the body fluid is obtained from silkworm, and a supernatant from the body fluid is used to recover FeIFN.

The recombinant silkworm nuclear polyhedrosis virus can be inactivated by incubating at a pH of 1 to 4 and at 4° C., for one day.

The FeIFN thus produced can be purified by a conventional procedure, for example, column chromatography. Also, for example, affinity chromatography are used. Particularly, the affinity chromatography preferably uses a carrier to which a blue pigment is bound (blue carrier), or a carrier to which copper is bound through a chelate linkage (copper chelate carrier). Although these carriers are used alone, preferably they are used in combination to improve the efficiency of the purification. In particular, a sequence of chromatography using a blue carrier and chromatography using a copper chelate carrier is preferably used.

As blue carriers, the following are used. The blue pigment is given the general name of CI reactive blue 2.

As examples thereof, a blue pigment marketed by Ciba-Geigy under the tradename of "Cibacron Blue F3GA" or "Cibacron Blue 3GA" and the like can be enumerated. As blue carriers to be used in chromatography, blue agarose gels marketed under the tradenames of "Blue Sepharose CL-6B" (Pharmacia Inc.) "Matrix Gel Blue A" (Amicon Inc.), "Affigel Blue" (Biorad Inc.), etc., and blue cellulose gels marketed under the tradenames of "Blue Trisacryl M" (LKB Inc.), "Blue Cellulofine" (Chisso Corp.), etc., are suitable and readily available.

As the copper chelate carrier, those prepared by treating carriers composed of exchangers having a chelating ability, e.g., biscarboxymethylamine group [—$N(CH_2COOH)_2$] and the like, and bonded to agarose, cellulose, polyacrylamide gel and the like with a solution of copper salt such as copper sulfate and the like can be enumerated, and among these carriers, an insoluble polysaccharide carrier such as "Chelating Sepharose" (manufactured by Pharmacia Inc.) or the like chelated with copper is preferably used.

The purification of an FeIFN by chromatography is carried out as follows. First, a solution containing FeIFN is adsorbed on the above carrier by contact. This adsorption may be carried out by either the batch method or column method, but the column method yields a higher adsorption efficiency. Then, the adsorbed FeIFN is eluted with an eluent.

The elution of the adsorbed FeIFN from the blue carrier is dependent on the pH value, the ionic strength, and the hydrophobicity of an eluent to be used. For example, the adsorbed FeIFN is eluted at a pH of 6 to 7 at a higher ionic strength. The ionic strength can be increased by raising the concentration of a buffer such as a phosphate buffer, acetate buffer, citrate buffer, borate buffer or the like, or by the addition of a neutral salt such as sodium chloride, potassium chloride or the like (0.2 to 1.0M). Where an eluent contains a solvent such as ethylene glycol, propylene glycol or the like, that weakens the hydrophobic interaction, an elution at a pH of 5 to 7 is possible.

The elution of the adsorbed FeIFN from the copper chelate carrier is usually carried out with an acidic buffer such as a phosphate buffer, acetate buffer, citrate buffer or the like, preferably at a pH of less than 5, but an elution at a much higher pH is possible at a higher ionic strength.

The composition, the concentration and the amount of an eluent is not particularly restricted. Namely, a composition effective for removing impure proteins contained in a crude FeIFN, a concentration required to maintain the pH, and the amount of an eluent required to substantially recover the adsorbed FeIFN are employed.

EXAMPLES

Hereinafter, the present invention will be described in more detail with reference to examples.

EXAMPLE 1

(1) Preparation of Feline cDNA Library

A feline cell LSA-D4-K17 (Reference 1) as a donor of poly(A)+RNA was proliferated by a spinner culture in 200 ml of an MEM-L15 medium (50% Eagle's MEM - 50% Leibovitz medium) containing 10% FBS. When the cell concentration reached $10^5$ to $10^6$/ml, TPA (12-O-tetradecanoylphorbol 13-acetate manufactured by Sigma Chemical Co.) was added, to a final concentration of 5 ng/ml, and after continuing the incubation for a further 20 hours, the cells were harvested by centrifugation. Poly(A)+RNAs were extracted from the harvested cells by a modified guanidiumthiocyanate method.

Namely, 3 to 5×10⁸ cells were suspended in 20 ml of 5 mM sodium citrate-0.5% sodium sarkosyl-0.1M mercaptoethanol-6M guanidiumthiocyanate and then homogenized by pipetting in and out the suspension with a 18 G injection needle 10 times. After pouring ½ vol. of 0.1 M EDTA (pH 7.5)-5.7M CsCl into a polyaroma centrifugal tube, the cell homogenate was layered thereon, the tube and contents were then centrifuged at 35,000 rpm at 20° C. for 20 hours in a Hitachi RPS40T rotor, and RNA fractions packed at the bottom of the tube were dissolved in 1 ml of TE (10 mM Tris-HCl-1 mM EDTA, pH 7.5). After mixing the solution with 0.1 ml of 3 M sodium acetate solution, the mixture solution was further mixed with 2.5 vol. of cold ethanol and then allowed to stand at −20° C. for 2 hours. A pellet formed at the bottom of the tube by centrifugation was dissolved in 1 ml of TE, incubated at 65° C. for 4 minutes, and then ice-cooled. After adding 1 ml of TE to the pellet treated as above, an equivalent volume of 1.0 M NaCl was mixed therein. The resultant mixture was passed through a column packed with 0.5 ml of oligo(dT) cellulose (type 3, manufactured by Collaborative Research Inc.) equilibrated with 0.5M NaCl-TE to make poly(A)+RNAs adsorb on the column. After washing the column with 10 ml of 0.5 M NaCl-TE, the adsorbed poly(A)+RNAs were eluted with 5 ml of TE. The poly(A)+RNAs pelletized according to the ethanolic precipitation method were dissolved in 30 μl of TE and preserved at −80° C/, and 300 μg of poly(A)+ RNA was obtained from 7×10⁸ cells.

The connection of a poly(A)+RNA to a plasmid vector, and the synthesis of cDNA, were carried out by using commercially available plasmid primers and linkers. Namely, 5 μl of 5 mg/ml poly(A)+RNA was poured into a 1.5-ml Eppendorf tube, and water was then added until the total volume reached 20 μl. After incubating the resultant solution at 65° C. for 3 minutes, the incubated solution was cooled to room temperature. To this incubated solution were added 4 μl of 0.3M Tris.HCl buffer (pH 8.3)-80 mM MgCl₂-0.3M KCl-3 mM dithiothreitol, 2 μg (3 μl) of oligo(dT)-tailed pcDV1 plasmid primer (manufactured by Pharmacia Inc.), 4 μl of mixture of each 25 mM dATP, dTTP, dGTP and dCTP, 2 μl of 10 mCi/ml [α-³²P]dCTP 3 μl of water, and 4 μl of 18 unit/μl reverse transcriptase (manufactured by Seikagaku Kogyo Co., Ltd.), in this order. The thus-prepared solution was incubated at 42° C. for 1 hour, to carry out the enzymatic reaction, and after terminating the reaction by the addition of 4 μl of 0.25M EDTA and 2 μl of 10% SDS, phenol-chloroform extraction was carried out. Thereafter, 40 μl of 4M ammonium acetate and 160 μl of ethanol were added to the separated aqueous layer obtained by phenol-chloroform extraction, and then cooled in dry ice for 15 minutes. The thus-treated aqueous layer was warmed to room temperature and then centrifuged in a microcentrifuge for 10 minutes. After decanting the supernatant, the pellet was dissolved in 20 μl of water, and to the resulting solution were added 20 μl of 4M ammonium acetate and 80 μl of ethanol, to again carry out the ethanol precipitation. The resultant pellet was washed with ethanol, dried, and then dissolved in 10 μl of water.

Then, to the resulting solution, were added 2 μl of 1.4M sodium cacodylate-0.3M Tris.HCl buffer (pH 6.8)-1 mM dithiothreitol, 1 μl of 200 μg/ml polyadenylic acid (manufactured by Seikagaku Kogyo Co., Ltd.), 1 μl of 20 mM CoCl₂, 1.4 μl of 1 mM dCTP, and 0.5 μl of 400 Ci/mmol (10 mCi/ml)[α-³²P]dCTP, in this order. After adding water until the total volume of the solution reached 20 μl, 0.8 μl of 27 unit/μl terminal nucleotidyl transferase was added thereto. The mixture solution was incubated at 37° C. for 5 minutes and the enzymatic reaction was terminated by placing the solution on ice. The number of dCMP residue added to the terminal was calculated to be 12 on average. Thereafter, nucleic acids were recovered from the reaction solution by the phenol-chloroform extraction method and double ethanol precipitation method.

These nucleic acids were dissolved in 40 μl of 10 mM Tris.HCl (pH 8.0)-60 mM NaCl-10 mM MgCl₂-1 mM 2-mercaptoethanol solution, to which 10 units of HindIII restriction enzyme was added, and after incubating the thus-prepared solution at 37° C. for 3 hours, DNAs were recovered by the phenol-chloroform extraction and double ethanol precipitation. The recovered DNAs were then washed with ethanol, dried, and dissolved in 10 μl of TE buffer.

To the resulting solution were added 5 μl of 2M NaCl, 81 μl of TE buffer and 4 μl of commercially available 3'-oligo(dG)-tailed pL1 linker (manufactured by Pharmacia Inc.), in this order, and after heating the mixture solution first at 65° C. for 5 minutes and then at 42° C. for 1 hour, the solution was ice-cooled. Then, to the ice-cooled solution, 100 μl of 0.2M Tris.Hcl buffer (pH 7.5)-40 mM MgCl₂-0.1M ammonium sulfate-1M KCl, 7 μl of 14 mM β-NAD, 50 μl of 1 mg/ml bovine serum albumin solution, and 6 μl of 1 mg/ml E. coli DNA ligase were added, in this order, and then water was added to bring the total volume to 1 ml. The resultant solution was incubated overnight at 12° C.

Then, to this reaction solution were added 2 μl of a mixed solution of each of 25 mM dATP, dGTP, dTTP and dCTP, 3 μl of 14 mM β-NAD, 0.7 μl of 35 unit/μl E. coli DNA polymeraseI(manufactured by Takara Shuzo Co. Ltd ). 2.4 μl of 2.5 unit/μl E. coli RNase H (manufactured by Takara Shuzo Co., Ltd.), and 4 μl of 1 mg/ml E. coli DNA ligase, in this order. After incubating the thus-prepared solution, first at 12° C. for 1 hour and then at 25° C. for 1 hour, the reaction solution was preserved at −20° C.

After carrying out the transformation reaction by adding 100 μl of the preserved reaction solution to 1 ml of a suspension of E. coli MC1061 (Reference 6), which was made to be competent according method of Reference 5, this reaction solution was poured into 250 ml of an LB medium containing 100 μg/ml ampicillin and then incubated overnight at 37° C, 0.7 ml of DMSO was added to 10 ml of this culture, and this portion was preserved at −80° C. as a cDNA library.

(2) Cloning

A portion of the thus-prepared cDNA library solution was spread on ten 9-cm diam. LB plates in such a manner that 1,000 to 2,000 colonies were formed in each plate, and after incubating these plates overnight at 37° C., the grown colonies were scraped off each petri dish and suspended in 10 ml of LB media, respectively. Thereafter, 3 ml of this suspension was mixed with 0.21 ml of DMSO and then cryopreserved. The remaining suspensions were respectively mixed with 100 ml of LB media containing 100 μg/ml ampicillin and then incubated overnight at 37° C. Thereafter, cells were harvested from the respective culture media, and plasmids were extracted and purified from the harvested cells according to the method of Reference 3. Then 30 μg of each these plasmids were subjected to the transient expression of COS1 cells (Reference 7) proliferated to the confluent state in 9-cm petri dishes by applying the DEAE dextran-transfection method whereby the FeIFN-producing ability of the respective plasmid DNA samples was determined.

Namely, after proliferating COS1 cells to the confluent state in 20 ml of an RPMI1640 (manufactured by GIBCO Inc.) medium containing 10% FBS in a 9-cm diam. petri dish, the medium was removed therefrom and 4 ml of an RPMI1640 medium containing a 7.5 μg/ml plasmid DNA sample, 50 mM Tris.HCl buffer (pH 7.4), 400 μg/ml DEAE-dextran (manufactured by Pharmacia Inc.) was poured in the petri dish and the incubation continued at 37° C. for 4 hours. The medium was exchanged with 4 ml of an RPMI1640 containing 150 μM chloroquine, and after a 3-hour incubation at 37° C., the medium was further exchanged with an RPMI1640 medium containing 10% FBS. After incubation at 37° C. for 3 days, the antiviral activity in the medium was determined. All of the RPMI1640 media mentioned above were used by adding 100 unit/ml penicillin and 100 μg/ml streptomycin thereto.

As a result, three out of ten culture media showed an antiviral activity of 20 unit/ml or more, and thus the concerned cryopreserved cDNA library solutions were screened for *Eschrichia coli* carrying a plasmid giving an antiviral activity-producing ability to the COS1 cell, in the following manner.

Namely, one out of three cryopreserved cDNA library solutions carrying plasmids producing the activity was diluted, spread on 10 LB plates each containing 100 μg/ml ampicillin in such a manner that approx. 600 colonies were formed per plate, and then incubated overnight at 37° C. After preparing replicas thereof as preservation plates, the cells were scraped from each plate, suspended in 5 ml of an LB media, and then each mixed with 100 ml of an LB media, respectively, containing 100 μg/ml ampicillin. After incubating the thus-treated cells overnight at 37° C, the resultant cells were harvested to extract and purify plasmids therefrom. Then 20 μg per petri dish of each of these 10 kinds of plasmids were subjected to the transient expression of COS1 cells according to the DEAE-dextran method, whereby the FeIFN-producing ability was determined.

As a result, it was determined that one out of ten plasmid samples had the FeIFN-producing ability, and thus 593 colonies in the concerned preservation plate were transplanted to fresh LB plates containing ampicillin, by using tooth picks, at a ratio of approx. 100 colonies per fresh plate. After an overnight incubation at 37° C., the cells scraped from each plate and then incubated overnight in 100 ml of an ampicillin containing-LB medium. Plasmids were extracted and purified from the harvested cells, and the antiviral activity-producing ability of each plasmid was determined by the transient expression method.

As a result, one plasmid sample was determined to have the antiviral activity-producing ability, and thus 100 colonies of the concerned preservation plate were each incubated in 2 ml of LB medium, and plasmids were extracted from these media. The antiviral activity-producing ability of each extracted plasmid was determined by the transient expression method, a plasmid having the highest antiviral activity-producing ability and an *Escherichia coli* carrying the plasmid were respectively designated as pFeIFN1 and *E. coli*(pFeIFN1), and this strain was deposited at the Fermentation Research Institute Agency of Industrial Science and Technology, 1-3, Higashi 1 chome Tsukuba-shi Ibaraki-Ken 305, Japan, (FERM BP-1633).

(3) Method of Antiviral Activity Determination

The antiviral activity was determined by using Vesicular Stomatitis Virus as a virus and a feline Fc9 cell (Reference 1) as a sensitive cell, by CPE method. As a standard reference, an HuIFN-α calculated in terms of NIH's human natural αIFN was used.

(4) Construction of Recombinant Plasmid Comprising DNA Coding for FeIFN (A) A plasmid pFeIFN1 was extracted from transformant *E. coli* (pFeIFN1) (FERM BP-1633) according to the procedure described in Reference 3, 20 μl of the plasmid pFeIFN1 was completely digested with restriction enzymes SfaNI and HincII, the resulting DNA fragments were separated by agarose gel electrophoresis, a DNA fragment of about 750 bp was recovered by electroelution to obtain about 2 μg of the DNA fragment, and thus a SfaNI-HincII DNA fragment containing a region coding for FeIFN was obtained.

Figure 2:
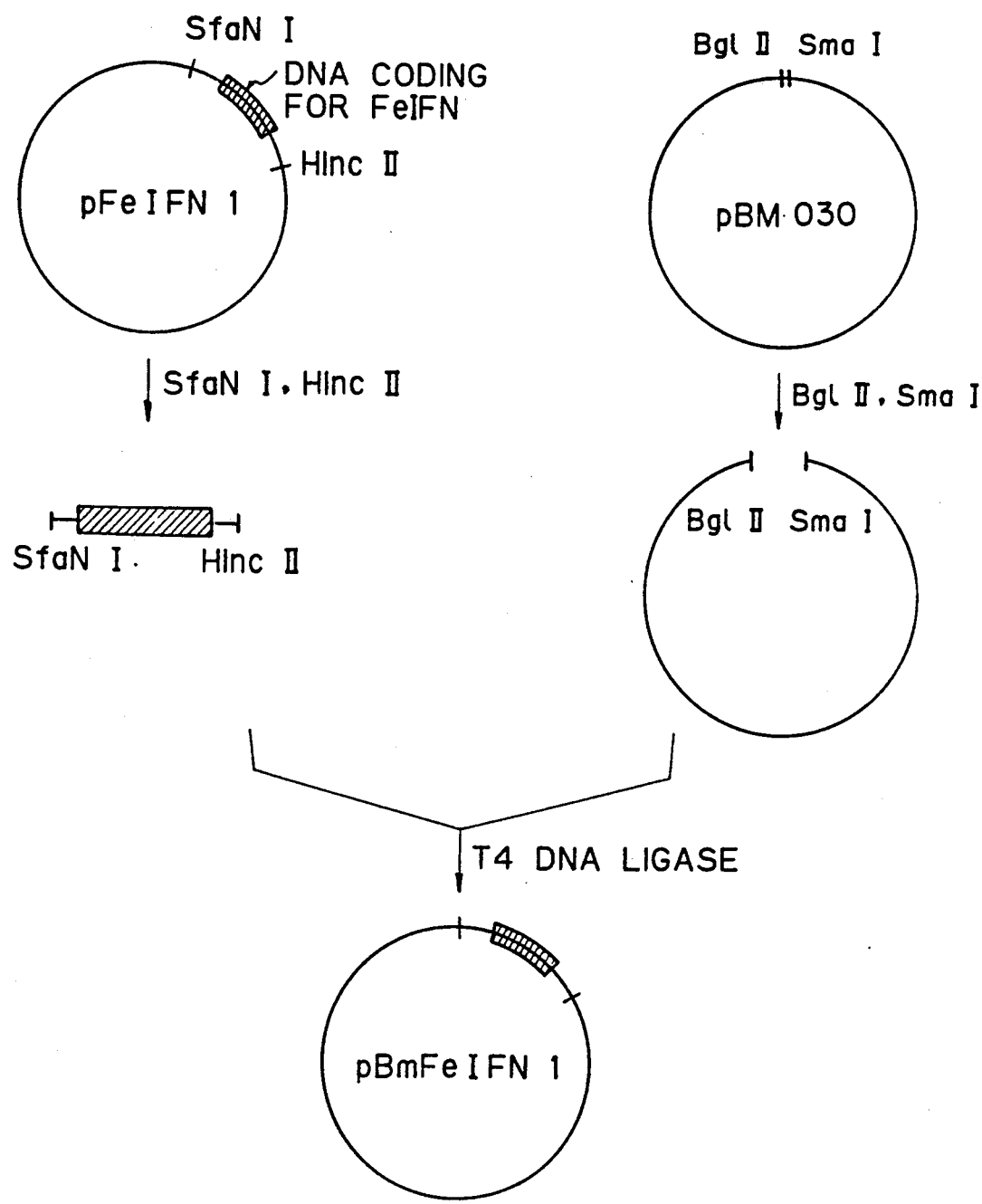
FIG. 2 represents a process for the construction of a recombinant plasmid pBmFeIFN1 comprising a DNA coding for the FeIFN.

On the other hand, 5 μg of a cloning vector pBM030 (Reference 2) was completely digested with restriction enzymes BglII and SmaI, and ligated with the above-prepared SfaNI-HincII fragment using a T4 DNA ligase. The reaction mixture was used to transform competent *E. coli* HB101 (Takara Shuzo Co., Ltd.), and the transformed *E. coli* cells were cultured on an LB plate containing 100 μg/ml ampicillin, to develop colonies from which a plasmid was extracted by a alkaline mini-screening method. The plasmids were analyzed by a restriction enzyme test using HindIII, to obtain a plasmid wherein a DNA fragment of about 750 bp is inserted into the cloning vector pBM030. The DNA segment in the plasmid of about a 100 base containing a initiation codon in DNA coding for FeIFN was sequenced to obtain a plasmid wherein a DNA fragment coding for FeIFN is inserted into the plasmid pBM030. This recombinant plasmid was designated pBmFeIFN1, and the construction process thereof is shown in FIG. 2.

(B) 100 μg of the plasmid pFeIFN1 was completely digested with a restriction enzyme HincII, treated with a bacterial alkaline phosphatase (BAP), and completely digested with a restriction enzyme BglI. The resulting DNA fragments were separated with agarose gel electrophoresis, a DNA fragment of about 700 bp was recovered by electroelution to obtain about 10 μg of the fragment, and thus a BglI-HincII DNA fragment containing a region coding for FeIFN was obtained.

Next, a double stranded DNA having a blunt end 3 bp upstream of the initiation codon ATG and extending downstreamwise to a BglI site was obtained. Namely, two oligomers, i.e., 34 mer (GGGCCACCAAGAAG-GAAGAGGGCAGCGCCATATT) and 37 mer (AA-TATGGCGCTGCCCTCTTCCTTCTTGGTGGCC-CTGG), were synthesized using a DNA synthesizer from Applied Biosystems, and after the 34 mer oligomer was treated with T4 Polynucleotide kinase, both obligomers were annealed by heating at 90° C. for 5 minutes, and then gradually cooled.

The BglI-HincII fragment prepared above and the double stranded DNA oligomer were ligated using a T4 DNA ligase, subjected to agarose gel electrophoresis, and a DNA fragment of about 740 bp was recovered by electroelution to obtain a DNA fragment containing a region coding for FeIFN.

A cloning vector pBM030 was cleaved with a restriction enzyme BglII, blunt-ended by using mung bean nuclease, and then treated with BAP to prevent self-ligation. The DNA fragment containing the FeIFN gene was treated with T4 Polynucleotide kinase, and ligated with the vector DNA using T4 DNA ligase.

Figure 3:
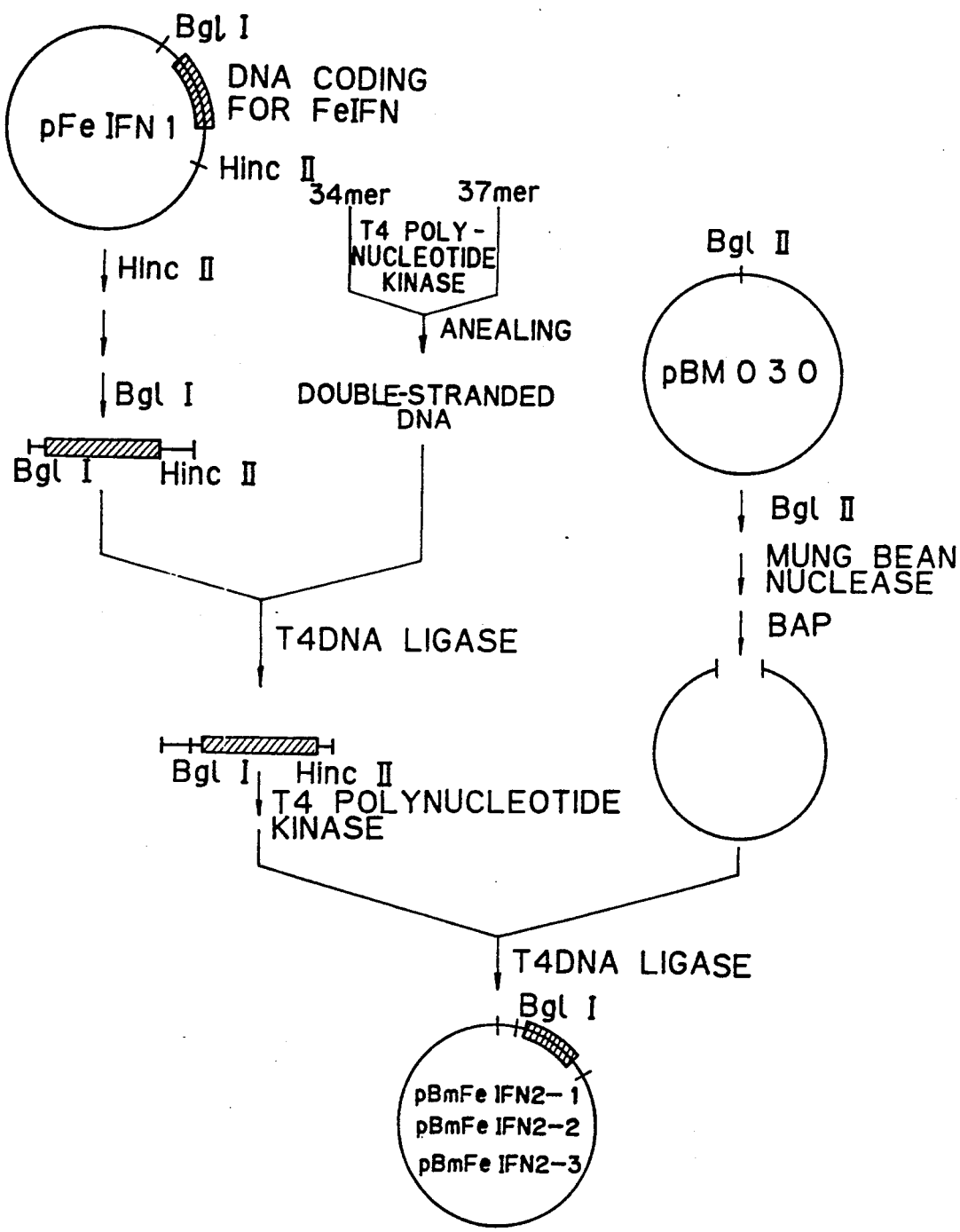
FIG. 3 represents a process for the construction of recombinant plasmids pBmFeIFN2-1, pBmFeIFN2-2 and pBmFeIFN 2-3, comprising a DNA coding for the FeIFN.

This reaction mixture was used to transform competent E. coli HB101 cells, and the transformed cells were cultured on an LB plate containing 100 μg/ml ampicillin, to develop colonies. Among the colonies, clones incorporating a DNA fragment of about 740 bp were selected by colony hybridization, using as a probe the above-mentioned BglI-HincII fragment containing DNA region coding for FeIFN, followed by a restriction enzyme analysis of plasmids extracted by an alkaline mini-screening method with BamHI and BglII. The plasmids were extracted according to the procedure described in Reference 3, and were sequenced in a region of about a 100 bases containing a initiation codon ATG, to obtain the desired plasmids. These recombinant plasmids were designated pBmFeIFN2-1, pBmFeIFN2-2, and pBmFeIFN2-3. A process for the construction of these three recombinant plasmids is shown in FIG. 3.

FIG. 4 shows the nucleotide sequences encompassing a initiation codon ATG, in the recombinant plasmid prepared in (A) and (B), i.e., pBmFeIFN1, pBmFeIFN2-1, pBmFeIFN2-2, and pBmFeIFN2-3 which encode FeIFN.

(5) Construction of Recombinant Silkworm Nuclear Polyhedrosis Virus Recombined with DNA Coding for FeIFN A recombinant virus was constructed according to a procedure described in Reference 2. Namely, to 2.5 ml of a solution containing 50 mM HEPES buffer (pH 7.1), 0.28 M NaCl, 0.7 mM $Na_2HPO_4$, and 0.7 mM $NaH_2PO_4$, was dropwise added 2.5 ml of DNA mixture [0.25 M $CaCl_2$, 10 μg of DNA of silkworm nuclear polyhedrosis virus BmNPV T3 (Reference 2), and 65 μg of DNA of a recombinant plasmid pBmFeIFN1, pBmFeIFN2-1, pBmFeIFN2-2, or pBmFeIFN2-3], and 0.5 ml of the resulting solution was added to a culture of about $3 \times 10^5$ BM-N cells (Reference 2) plate-cultured in 5 ml of TC-10 medium (Reference 4) supplemented with 10% FBS in a 25 $cm^2$ flask, to introduce the DNA into the silkworm cell. After 20 hours, the medium was exchanged with a fresh medium, and after a further culturing for 5 days, the culture broth was recovered. The culture broth was centrifuged to obtain a clear supernatant, which was then diluted and added to a culture of plate-cultured BM-N cells, followed by culturing for 7 days. Cultures in which viral infection was microscopically observed and the polyhedra was not formed were selected (limiting dilution method). The limiting dilution method was twice repeated to clone recombinant viruses, and the resulting recombinant viruses comprising DNA coding for FeIFN were designated BmFeIFN1, BmFeIFN2-1, BmFeIFN2-2, and BmFeIFN2-3, respectively, corresponding to the starting recombinant plasmids. The BmFeIFN1 was deposited with the European Collection of Animal Cell Cultures, PHLS Centre for Applied Microbiology & Research Porton Down Salisbury SP4 OJG UK under the Budapest Treaty on Jun. 27, 1989 as accession No. V89062701.

(6) Preparation of Recombinant Virus Solution

To about $3 \times 10^6$ BM-N cells plate-cultured in 15 ml of TC-10 medium supplemented with 10% FBS in 75 $cm^2$ flask was added 50 μl of a culture medium of BM-N cells containing one of the recombinant viruses cloned in the above (5). Then, after culturing at 27° C. for 5 days, the culture broth was centrifuged at 3,000 rpm for 5 minutes to obtain the supernatant as a recombinant virus solution. Each virus solution was diluted to $10^{-7}$ of the original concentration, and 1 ml of the diluted virus solution was added to a culture of BM-N cells, which were then cultured at 27° C. for 7 days. As a result, a viral infection was observed of BM-N cells in all of the cultures.

(7) Production of FeIFN in Established Silkworm Cells

Four recombinant virus solutions obtained in the above (6) were separately treated as follows. First, 0.5 ml of the virus solution was added to about $3 \times 10^6$ BM-N cells plate-cultured in a TC-10 medium supplemented with 10% FBS in a 25 $cm^2$ flask. After 30 minutes, the culture medium was exchanged with 5 ml of fresh TC-10 medium supplemented with 10% FBS, and culturing was carried out at 27° C. for 3 days. The culture broth was the centrifuged to obtain a supernatant, and the antiviral activity of the supernatant was determined. The results are shown in Table 1.

(8) Production of FeIFN in Established Silkworm Cells Grown in a Serum-Free Medium To about $3 \times 10^6$ BM-N cells plate-cultured in TC-10 medium supplemented with 4 g/l yeast extract, 1 g/l Pluronic polyol F-68 (BASF), 10 mg/l codfish oil, 25 mg/l Tween 80, 4.5 mg/l choresterol, and 2 mg/l tocopherol acetate instead of FBS, in a 25 $cm^2$ flask, was added 0.5 ml of a recombinant virus BmFeIFN1 solution. After 30 minutes, the culture medium was exchanged with a fresh medium having the same composition, and culturing was carried out at 27° C. for 3 days. The culture broth was centrifuged to obtain a supernatant, and the antiviral activity thereof was then determined. FeIFN was produced in an amount of $5.8 \times 10^5$ units/ml culture broth.

(9) Production of FeIFN in Established Silkworm Cells by Suspension Culture

BM-N cells were cultured in 150 ml of TC-10 medium supplemented with 10% FBS, in a 500 ml spinner flask at 80 rpm and 27° C. When the cell concentration reached $5.3 \times 10^5$ cells/ml, 1 ml of the recombinant virus BmFeIFN1 solution prepared in the above (6) was added to the culture, and the suspension culture was continued at 27° C. for 4 days. The culture broth was recovered and centrifuged to obtain a supernatant, and the antiviral activity of the supernatant then determined. FeIFN was produced in an amount of $2.1 \times 10^5$ units/ml culture broth.

(10) Production of FeIFN in the Body of Silkworm

A virus solution of four recombinant viruses, prepared in the above (6), were separately tested as follows. First, 50 μl/head of the virus solution was injected into larvae of silkworm at the second day of the fifth instar stage, and the larvae were kept on a commercial artificial feed (VITA-SILK Co., Ltd.) at 25° C. for 4 days. The uropod was cut and the body fluid was collected in an ice-cooled Eppendorf tube, which was then centrifuged to obtain a supernatant, and the antiviral activity of the supernatant was determined. The results are shown in Table 1.

TABLE 1

| Recombinant virus tested | FeIFN produced (units/ml) | |
|---|---|---|
| | Culture supernatant of BM-N cells | Body fluid of silkworm |
| BmFeIFN1 | $1.9 \times 10^6$ | $7.7 \times 10^7$ |
| BmFeIFN2-1 | $1.3 \times 10^6$ | $4.7 \times 10^7$ |
| BmFeIFN2-2 | $1.4 \times 10^6$ | $5.5 \times 10^7$ |
| BmFeIFN2-3 | $1.7 \times 10^6$ | $6.2 \times 10^7$ |

EXAMPLE 2

(1) Construction of Recombinant Plasmid Comprising DNA Coding for FeIFN

Figure 5A:
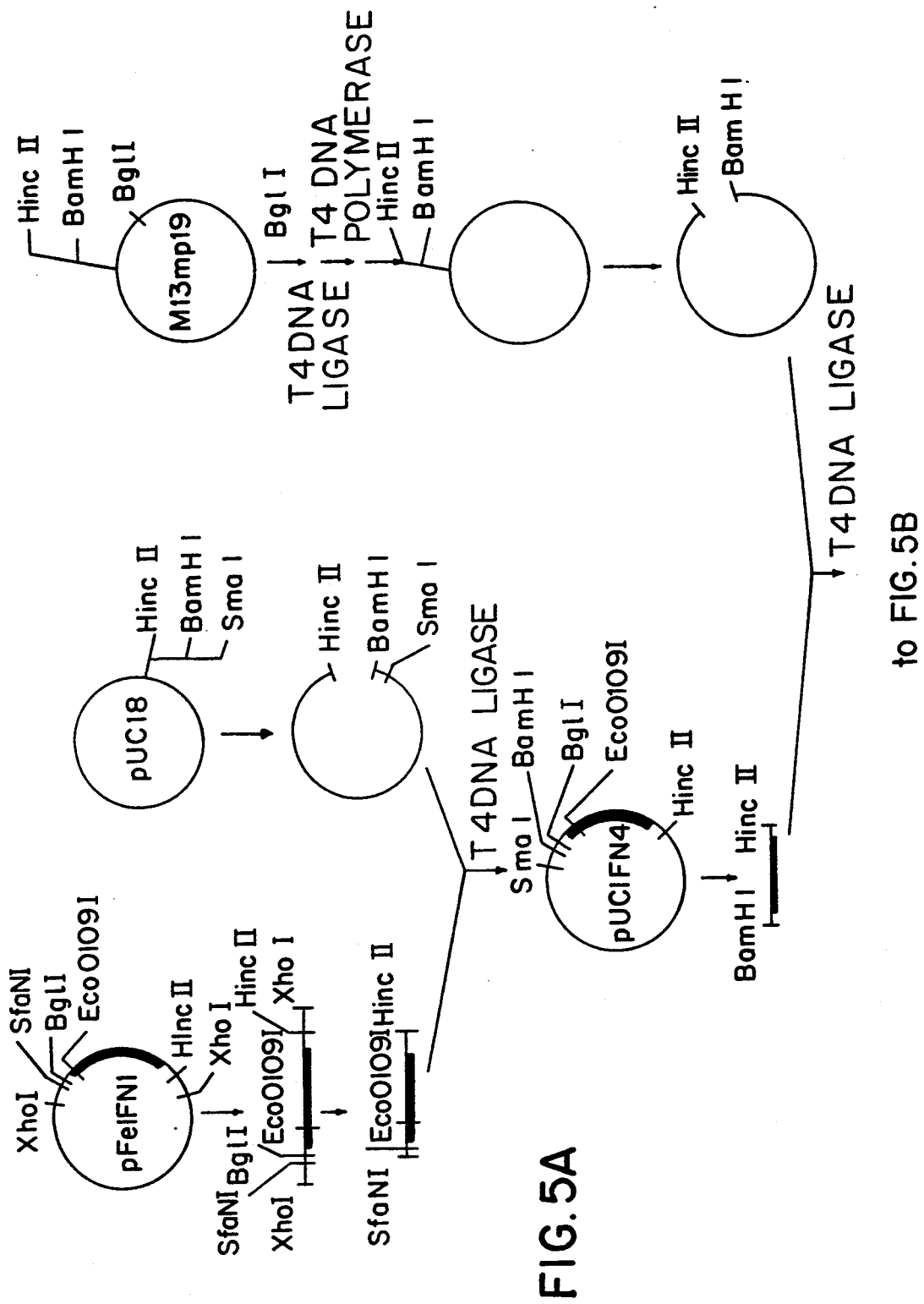
FIG. 5 (parts A and B) represents a process for the construction of a recombinant plasmid pYU871 comprising a DNA coding for the FeIFN.
Figure 5B:
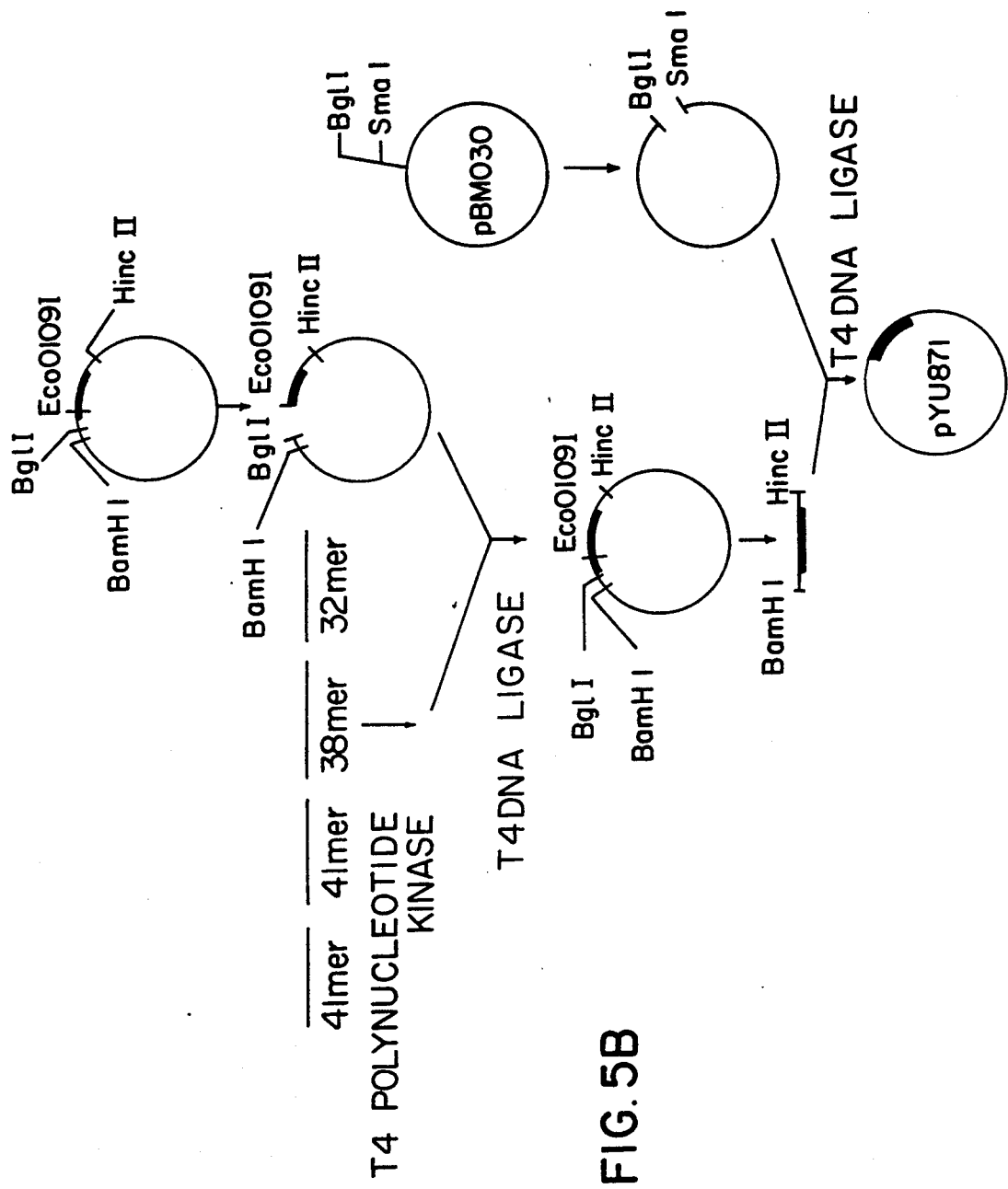

A recombinant plasmid comprising DNA coding for FeIFN was constructed from the plasmid pFeIFN1 shown in FIG. 1, by a process shown in FIG. 5.

Namely, 50 μg of the plasmid pFeIFN1 was completely digested with a restriction enzyme XhoI, the resulting DNA fragments were separated by agarose gel electrophoresis, and a DNA fragment of about 1.2 kb was recovered by electroelution to obtain about 10 μg of the DNA. Next, 10 μg of this DNA fragment was completely cleaved with restriction enzymes SfaNI and HincII, and among the resulting DNA fractions, about 3 μg of a DNA fraction having about 750 bp in length was recovered as described above. Accordingly, a SfaNI-HincII fragment containing FeIFN structural gene was obtained. This fragment was ligated with a commercially available plasmid pUC18 (Takara Shuzo Co. Ltd.) which had been cleaved with restriction enzymes BamHI and HincII, using a T4 DNA ligase, to construct pUCIFN4.

Next, 25 μg of the pUCIFN4 was completely digested with restriction enzymes BamHI and HincII, the resulting DNA fragments were separated by agarose gel electrophoresis, and a DNA fragment of about 0.7 kb was recovered by electroelution to obtain about 2 μg of the fragment.

Next, 5 μg of a commercially available M13mp19 RF DNA (Takara shuzo Co. Ltd.) was completely digested by using a restriction enzyme BglI, blunt-ended with T4 DNA polymerase, and then self-ligated using a T4 DNA ligase to construct a M13 vector lacking a BglI cleavage site. This vector was completely digested with restriction enzymes BamHI and HincII, and ligated with the above-prepared 0.7 kb BamHI-HincII fragment. Next, 10 μg of this recombinant DNA was completely cleaved with restriction enzymes BglI and Eco0109I, treated with bacterial alkaline phosphatase (Takara Shuzo Co. Ltd.), DNA fragments were separated by agarose gel electrophoresis, and a DNA fragment of about 7.9 kb was recovered by electroelution.

Next, a double stranded DNA starting from a BglII site and ending at an Eco0109I was synthesized. Namely, the following four oligonucleotides:

41 mer (TGGCGCTGGGCTGCAACTCCGTCTGCGTGCTGGGCTGTGAC),
32 mer (CTGCCTCAGACCCACGGCCTGCTGAACAGGAG),
38 mer (GCCCAGCACGCAGACGGAGTTGCAGCCCAGCGCCACCA),
41 mer (GCCCTCCTGTTCAGCAGGCCGTGGGTCTGAGGCAGGTCACA)

were synthesized by a DNA synthesizer (Applied Biosystems) were mixed, treated with T4 polynucleotide kinase (Takara Shuzo Co. Ltd.), and subjected to annealing by heating at 90° C. for 2 minutes, and allowed to cool. This double-stranded DNA was ligated with the above-prepared 7.9 kb BglI-Eco0109I fragment using a T4 DNA ligase, 20 μg of the resulting DNA was completely digested with restriction enzymes BamHI and HincII, the resulting DNA fragments were separated by agarose gel electrophoresis, a DNA fragment of about 750 bp was recovered by electroelution to obtain about 2 μg of the DNA fragment, and thus thereby, a BamHI-HincII DNA fragment containing a region coding for FeIFN was obtained.

On the other hand, 5 μg of a cloning vector pBM030 (Reference 2) was completely digested with restriction enzymes BglII and SmaI, and ligated with the above-prepared BamHI-HincII fragment using a T4 DNA ligase. The reaction mixture was used to transform competent E. coli HB101 (Takara Shuzo Co. Ltd.), and the transformed E. coli cells were cultured on an LB plate containing 100 μg/ml ampicillin, to develop colonies from which a plasmid was extracted by a alkaline miniscreening method. The plasmids were analyzed by a restriction enzyme test using HindIII, to obtain a plasmid wherein a DNA fragment of about 750 bp is inserted into the cloning vector pBM030. The DNA segment coding for FeIFN in the plasmid was sequenced to identify the desired plasmid. This recombinant plasmid was designated pYU871. A nucleotide sequence of the DNA in pYU871, coding for FeIFN, is shown in FIG. 6.

(2) Construction of Recombinant Silkworm Nuclear Polyhedrosis Virus Recombined with DNA Coding for FeIFN A recombinant virus was constructed according to a procedure described in Reference 2. Namely, to 2.5 ml of solution containing 50 mM HEPES buffer (pH 7.1), 0.28 M NaCl, 0.7 mM $Na_2HPO_4$, and 0.7 mM $NaH_2PO_4$ was dropwise added 2.5 ml of a DNA mixture [0.25 M $CaCl_2$, 10 μg of DNA of a silkworm nuclear polyhedrosis virus BmNPV T3 (Reference 2) and 65 μg of DNA of a recombinant plasmid pYU871], and 0.5 ml of resulting solution was added to a culture of about $3 \times 10^5$ BM-N cells (Reference 2) plate-cultured in 5 ml of a TC-10 medium (Reference 4) supplemented with 10% FBS in a 25 $cm^2$ flask, to introduce the DNA into the silkworm cell. After 20 hours, the medium was exchanged with a fresh medium, and after a further culturing for 5 days, the culture broth was recovered. The culture broth was centrifuged to obtain a clear supernatant, which was then diluted and added to a culture of plate-cultured BM-N cells, followed by culturing for 7 days. Cultures in which a viral infection was microscopically observed and the polyhedra was not formed were selected (limiting dilution method). After the limiting dilution method was repeated five times, the recombinant virus was cloned by a plaque method.

Namely, $5 \times 10^6$ of BM-N cells were cultured in a plastic petri dish having a diameter of 60 mm, and after the culture broth was removed, 0.5 ml/plate of a virus solution was added. After incubation at 27° C. for one hour, the virus solution was removed, and 5 ml of TC-10 medium containing 0.75% Sea Plaque Agarose (FMC) and 5% fatal bovine serum was added. After the agarose was solidified, culturing was carried out at 27° C. for 4 to 6 days. Next, 2.5 ml of TC-10 medium containing 0.01% neutral red was overlayied on the above culture medium containing agarose, and incubation was carried out at 27° C. for one day. An agarose portion containing a transparent plaque in which polyhedra has not formed was aspirated with a Pasteur's pipette and suspended in a small amount of a culture medium, and the plaque purification was further repeated twice to clone a recombinant virus. The recombinant virus thus constructed, which contains DNA coding for FeIFN, was designated rBNV100.

(3) Preparation of Recombinant Virus Solution

To about $3 \times 10^6$ BM-N cells plate-cultured in 15 ml of a TC-10 medium supplemented with 10% FBS in 75 cm$^2$ Flask, was added 50μl of a culture medium of BM-N cells containing the recombinant viruses cloned in the above (2). After culturing at 27° C. for 5 days, the culture broth was centrifuged at 3,000 rpm for 5 minutes to obtain the supernatant as a recombinant virus solution. The virus solution was diluted to $10^{-7}$ of the original concentration, and 1 ml of the diluted virus solution was added to a culture of BM-N cells, which were then cultured at 27° C. for 7 days. As a result, a viral infection was observed for BM-N cells in the culture.

(4) Production of FeIFN in Established Silkworm Cells

The recombinant virus solution obtained in the above (3) was treated as follows. First, 0.5 ml of the virus solution was added to about $3 \times 10_6$ BM-N cells plate-cultured in a TC-10 medium supplemented with 10% FBS in a 25 cm$^2$ flask. After 30 minutes, the culture medium was exchanged with 5 ml of fresh TC-10 medium supplemented with 10% FBS, and culturing was carried out at 27° C. for 3 days. The culture broth was centrifuged to obtain a supernatant, and the antiviral activity of the supernatant was determined. The results are shown in Table 2.

(5) Production of FeIFN in the Body of Silkworm

A virus solution of a recombinant virus, prepared in the above (3), was tested as follows. First, 50 μl/head of the virus solution was injected into larvae at the second day of the fifth instar stage, and the larvae were kept on a commercial artificial feed (Vitasilk Hanbai Kabushiki Kaisha) at 25° C. for 4 days. The uropod was cut and the body fluid was collected in an ice-cooled Eppendorf tube, which was then centrifuged to obtain a supernatant, and the antiviral activity of the supernatant was determined. The results are shown in Table 2.

TABLE 2

| Recombinant virus tested | FeIFN produced (units/ml) | |
|---|---|---|
| | Culture supernatant of BM-N cells | Body fluid of silkworm |
| rBNV100 | $1.7 \times 10^6$ | $6.8 \times 10^7$ |

(6) Inactivation of Recombinant Silkworm Nuclear Polyhedrosis Virus

The body fluid of a silkworm, obtained in the above (5) and containing $4 \times 10^9$ TCID$_{50}$/ml of recombinant silkworm nuclear polyhedrosis virus, was adjusted to a pH of 1.5 with 0.1 N hydrochloric acid and maintained at 4° C. for one day. After neutralization of solution with 2N NaOH, 1 ml of the solution was added to a culture broth of BM-N cells, and the cells were not infected with the virus.

The body fluid of a silkworm, which has been acidated with HCl to inactivate the recombinant virus and then neutralized with NaOH solution, was used as a crude FeIFN solution.

(7) Purification of FeIFN by Blue-Carrier

First, 560 ml of the crude FeIFN solution prepared in the above (6) having an FeIFN activity of $1.3 \times 10^6$ U/ml and a specific activity of $4.7 \times 10^5$ U/mg protein was applied to a column containing 27 ml of "Blue Sepharose (Fast Flow Type)". After washing the column with a 20 mM phosphate buffer (pH 8) containing 0.5M NaCl, the adsorbed FeIFN was eluted with 490 ml of mM phosphate buffer (pH 8) containing 1 M NaCl. The eluted FeIFN fraction contained an FeIFN activity of $1.4 \times 10^6$ U/ml and showed a specific activity of $3.5 \times 10^7$ U/mg protein. The recovery yield of FeIFN activity was 94%, and the specific activity was increased 74 fold.

(8) Purification of FeIFN Using Copper Chelate Carrier

First, 310 ml of the FeIFN elute from the blue carrier described in the above (7) was directly applied to a column containing 5 ml of Sepharose, to which copper has been bonded through a chelate linkage, the column was washed with 50 mM acetate buffer (pH 4.2) containing 0.5 M NaCl and 50 mM acetate buffer (pH 3.9) containing 0.5 M NaCl, and the adsorbed FeIFN was eluted with 33 ml of a 50 mM acetate buffer (pH 3.6) containing 0.5 M NaCl. The eluted FeIFN fraction contained an FeIFN activity of $1.1 \times 10^7$ U/ml and showed a specific activity of $1.2 \times 10^8$ U/mg protein. The recovery yield was 84%, and the specific activity was increased 3.4 fold in this step.

(9) Determination of Molecular Weight of FeIFN

The molecular weight of the FeIFN was determined for the FeIFN sample obtained in the above (8), by SDS-polyacrylamide gel electrophoresis.

Namely, 1 μg of FeIFN sample was boiled in a solution containing 4% SDS and 10% 2-mercaptoethanol and applied to a gel consisting of a concentration gel having an acrylamide concentration of 5% and a separation gel having an acrylamide concentration of 15%, electrophoresis was carried out using a Rapidas Minislab gel electrophoresis apparatus (ATTO), at 15 mA. As a molecular weight standard, the SDS-PAGE Standards, Low Range (BIO-RAD) was used. After electrophoresis, the gel was sequentially shaken in 40% methanol- 10% acetic acid and 10%ethanol -5% acetic acid, in this order, for 30 minutes each, and then shaken in a dye solution containing 0.05% Coomassie R250 (BIO-RAD), 25% isopropanol, and 10% acetic acid, for 3 hours. The gel was decolored and the molecular weight was calculated. The molecular weight of FeIFN was 25,000.

(10) Determination of Amino Acid Sequence of FeIFN

The amino acid sequence of 10 amino acids from the N-terminus was determined using 100 μg of FeIFN obtained in the above (8) and an amino acid sequencer (Applied Biosystems). The N-terminal sequence was as follows:

Next, about 1 mg of FeIFN obtained in the above (8) was highly purified by reversephase high performance liquid chromatography (HPLC) using a Vydac $C_{18}$ column (The Sep/a/ra/tions Group) and an elution condition of a 30–50% acetonitrile linear gradient for 20 minutes. The purified FeIFN was reduced with mercaptoethanol in the presence of 8 M urea to cleave disulfide bonds, the formed cystein residues were modified with 4-vinylpiridine, and the product was desalted. The derivatized FeIFN was digested by lysyl endopeptidase at 37° C. overnight, and the resulting peptides were isolated by reversephase HPLC. using a 5–55% acetonitrile linear gradient for 50 minutes. The longest peptide was re-digested with trypsin, and the resulting peptides were separately isolated. Each peptide was hydrolyzed with HCl and the amino acid composition was determined by an amino acid analyzer (Hitachi). On the other hand, the amino acid sequence was determined by an amino acid sequencer for each peptide. The amino acid sequence of each peptide was determined from the results of the amino acid composition analysis and sequence analysis. The amino acid sequence of FeIFN was determined by considering the amino acid sequence of N-terminal 10 amino acids of FeIFN and the DNA sequence coding for FeINF as described above. The amino acid sequence of FeIFN is shown in FIG. 6.

(11) Determination of Isoelectric Point of FeIFN

For the FeIFN obtained in the above (8), an isoelectric point was determined.

Namely, using PhastSystem (Pharmacia), 1.6 μg of FeIFN which has been boiled in the presence of 4% SDS and 10% 2-mercaptoethanol was applied to an electrophoretic gel IEF-3-9 as described in the above (9). As the isoelectric point makers, LKB pH 3-10 (Pharmacia) were used. After the electrophoresis, the gel was stained with silver. The isoelectric point was 6.

(12) Analysis of Sugar Chain of FeIFN

FeIFN purified in the above (8) was subjected to SDS-polyacrylamide gel electrophoresis, and the gel was PAS-stained to analyze the sugar chain of the FeIFN.

Namely, 20 μg of FeIFN was applied to a electrophoretic gel having an acrylamide concentration gradient of 4–20%, i.e., TEFCO mini (TEFCO), after carrying out the SDS-polyacrylamide gel electrophoresis using as molecular weight makers SDS-PAGE Standards, Low Range (BIO-RAD) and Rainbow Markers (Amersham), the gel was stained according to a conventional procedure by a Coomassie stain and PAS stain. Both the Coomassie stain and PAS stain showed a band corresponding to a molecular weight of 25,000. This result confirmed the presence of sugar chains.

(13) Antiviral Effects of FeIFN

To 100 μl of a culture broth of feline cells Fc9 (Reference 1) or CRFK (Reference 1) grown confluently in a 96 well plate, was added 100 μl of $5.8 \times 10^5$ U/ml FeIFN obtained in the above (8) or a medium, and the whole was incubated in a carbon dioxide incubator at 37° C. for 24 hours. After removing the culture broth, 150 μl of feline calicivirus FRI-14 (C14) solution having $10^{5.5} TCID_{50/ml}$ was added, and further incubation was carried out at 37° C. for 24 hours.] After removing the virus, cells adhering to the bottom of well were stained by crystal violet, and the absorbance at 590 nm ($OD_{590}$) was measured. The results are shown in Table 3.

TABLE 3

| Cells | $OD_{590}$ | |
|---|---|---|
| | FeIFN − | FeIFN + |
| Fc9 | 0.50 | 0.90 |
| CRFK | 0.50 | 1.52 |

As seen from the above, the FeIFN prepared according to the present invention exhibits antiviral activity against feline calicivirus.

References:

1. J. K. Yamamoto et al.: Vet. Immunol. and Immunopathol., 11, 1–19, (1986).
2. T. Horiuchi et al.: Agric. Biol. Chem., 51, 1573–1580, (1987).
3. T. Maniatis et al. ed.: Molecular Cloning, A Laboratory Manual, (1982) p86–96, Cold Spring Harbor Laboratory, New York.
4. G. R. Gardiner and H. Stockdale: J. Invertebrate Pathology, 25, 363–370, (1975).
5. D. Hanahan: J. Mol. Biol., 166, 577–580, (1983).
6. M. J. Casadaban et al.: J. Mol. Biol., 138, 179–207 (1980).
7. Y. Gluzman: Cell, 23, 175–182 (1981).

We claim:

1. A process for production of a recombinant silkworm nuclear polyhedrosis virus constructed by a gene recombination of DNA coding for a protein of feline interferon and a silkworm polyhedrosis virus, comprising the steps of:
   cotransfecting a recombinant plasmid having a gene coding for a protein of feline interferon and a silkworm nuclear polyhedrosis virus DNA into established silkworm cells; and
   cloning the desired recombinant virus.

2. A process according to claim 1, wherein the plasmid is selected from the group consisting of pBmFeIFN1, pBmFeIFN2-1, pBmFeIFN2-2, pBmFeIFN2-3, and pYU871.

3. A process according to claim 1, wherein the established silkworm cell is a BM-N cell.

4. A process according to claim 1, wherein said recombinant plasmid is a plasmid which comprises the BglI-HincII restriction fragment of plasmid pFeIFN1 which includes DNA encoding the Feline Interferon protein ligated into a plasmid suitable for the expression of Feline Interferon in insect cells.

5. A process according to claim 4, wherein said recombinant plasmid is a plasmid which further comprises the BglI-HincII restriction fragment of plasmid pFeIFN1 which includes DNA encoding the Feline Interferon protein ligated to a linker,

```
5'—   gggccaccaagaaggaagagggcagcgccatatt—3'
3'—ggtcccggtggttcttccttctcccgtcgcggtataa   —5'
``` which attaches tot he BfgII end of the BglI-HincII restriction fragment.

6. A process according to claim 1, wherein said recombinant plasmid is a plasmid which comprises the EcoO109I-HincII restriction fragment of plasmid PFeIFN1 which includes DNA encoding the Feline Interferon protein ligated to the linker

```
acccacggcctgctgaacaggag   —3'
tgggtgccggacgacttgtcctcccg—5'.
```

7. A process according to claim 6, wherein said recombinant plasmid is a plasmid which further comprises the small SfaNI-BglI fragment which is upstream of the FeIFN coding region of plasmid PFeIFN1, as shown in FIG. 5, ligated to the BglII site of the linker DNA so as to form a segment of DNA bounded by a BamHI site and HincII site which contains the nucleotides encoding the Feline Interferon protein.

8. A process according to claim 7, wherein the BAmHI-HincII fragment containing the nucleotides encoding the Feline Interferon protein is ligated to a plasmid suitable for expression of Feline Interferon in insect cells.

9. A process according to claim 8, wherein the said plasmid suitable for expression of Feline Interferon in insect cells is the plasmid PBM030.

10. A recombinant silkworm nuclear polyhedrosis virus according to claim 5, which is BMFeIFN1.

11. A recombinant silkworm nuclear polyhedrosis virus according to claim 5, which is BmFeIFN2-1.

12. A recombinant silkworm nuclear polyhedrosis virus according to claim 5, which is BmFeIFN2-2.

13. A recombinant silkworm nuclear polyhedrosis virus according to claim 5, which is BmFeIFN2-3.

14. A recombinant silkworm nuclear polyhedrosis virus according to claim 5, which is rBNV100.

15. A recombinant silkworm nuclear polyhedrosis virus containing a DNA coding for a protein of feline interferon.

16. A recombinant silkworm nuclear polyhedrosis virus selected from the group consisting of BmFeIFN1 (ECACC V89062701), BmFeIFN2-1, BmFeIFN2-2, BmFeIFN2-3, and rBNV100.

* * * * *